US009696268B2

(12) United States Patent
Sinha et al.

(10) Patent No.: US 9,696,268 B2
(45) Date of Patent: Jul. 4, 2017

(54) AUTOMATED DECISION-BASED ENERGY-DISPERSIVE X-RAY METHODOLOGY AND APPARATUS

(71) Applicant: KLA-Tencor Corporation, Milpitas, CA (US)

(72) Inventors: Harsh Sinha, Milpitas, CA (US); Dmitry Spivak, Ballston Spa, NY (US); Huina Xu, Milpitas, CA (US); Hong Xiao, Pleasanton, CA (US); Rohit Bothra, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/919,563

(22) Filed: Oct. 21, 2015

(65) Prior Publication Data

US 2016/0116425 A1      Apr. 28, 2016

Related U.S. Application Data

(60) Provisional application No. 62/069,048, filed on Oct. 27, 2014, provisional application No. 62/159,180, (Continued)

(30) Foreign Application Priority Data

Jun. 19, 2015    (IN) .......................... 3080/CHE/2015

(51) Int. Cl.
*G01N 23/00*      (2006.01)
*G01N 23/22*      (2006.01)
(Continued)

(52) U.S. Cl.
CPC .......... *G01N 23/2252* (2013.01); *H01J 37/20* (2013.01); *H01J 37/28* (2013.01); *H01J 2237/22* (2013.01); *H01J 2237/2806* (2013.01)

(58) Field of Classification Search
USPC ........ 250/306, 307, 310, 311, 442.11, 443.1, 250/370.09, 399, 492.3, 526, 422.11, 52;
(Continued)

(56) References Cited

U.S. PATENT DOCUMENTS 5,065,020 A    11/1991  Kanda
5,263,075 A    11/1993  McGann et al.
(Continued)

FOREIGN PATENT DOCUMENTS

EP    2 237 306 B1    6/2010
JP     2002083564 A    3/2002
JP       4881307 B2    2/2012

OTHER PUBLICATIONS

PCT International Search Report for Application No. PCT/US2015/057455, mailed Feb. 1, 2016 (Feb. 1, 2016), 3 sheets.
(Continued)

*Primary Examiner* — Bernard Souw
(74) *Attorney, Agent, or Firm* — Okamoto & Benedicto LLP (57) ABSTRACT

One embodiment relates to a method for automated review of defects detected in a defective die on the target substrate. The method includes: performing an automated review of the defects using an secondary electron microscope (SEM) so as to obtain electron-beam images of the defects; performing an automated classification of the defects into types based on morphology of the defects as determined from the electron-beam images; selecting defects of a specific type for automated energy-dispersive x-ray (EDX) review; and performing the automated EDX review on the defects of the specific type. In addition, automated techniques are disclosed for obtaining an accurate reference so as to improve the usefulness of the EDX results. Furthermore, an automated method of classifying the defects based on the EDX results is disclosed which provides a final pareto that com-
(Continued)

bines both morphological and elemental information. Other embodiments, aspects and features are also disclosed.

16 Claims, 9 Drawing Sheets

Related U.S. Application Data filed on May 8, 2015, provisional application No. 62/171,698, filed on Jun. 5, 2015, provisional application No. 62/204,325, filed on Aug. 12, 2015.

(51) Int. Cl.
*G01N 23/223* (2006.01)
*G01T 1/36* (2006.01)
*G01N 23/225* (2006.01)
*H01J 37/28* (2006.01)
*H01J 37/20* (2006.01)

(58) Field of Classification Search
USPC ......... 378/1, 5, 45, 46, 54, 58, 210, 63, 101
See application file for complete search history.

(56) References Cited

U.S. PATENT DOCUMENTS

| | | | |
|---|---|---|---|
| 5,656,812 A * | 8/1997 | Takahashi | H01J 37/256 250/310 |
| 6,072,178 A | 6/2000 | Mizuno | |
| 6,259,960 B1 * | 7/2001 | Inokuchi | G01N 21/9501 250/310 |
| 6,407,386 B1 | 6/2002 | Dotan et al. | |
| 6,423,557 B1 | 7/2002 | Steffan et al. | |
| 6,442,233 B1 | 8/2002 | Grodzins et al. | |
| 6,479,818 B1 | 11/2002 | McCarthy et al. | |
| 6,753,261 B1 | 6/2004 | Phan et al. | |
| 6,787,773 B1 | 9/2004 | Lee | |
| 6,855,930 B2 * | 2/2005 | Okuda | G06T 7/0004 250/310 |
| 6,870,169 B2 | 3/2005 | Obara et al. | |
| 6,921,672 B2 | 7/2005 | Satya et al. | |
| 7,092,485 B2 | 8/2006 | Kravis | |
| 7,132,652 B1 | 11/2006 | Testoni | |
| 7,205,555 B2 * | 4/2007 | Okuda | G06T 7/0004 250/306 |
| 7,474,986 B2 * | 1/2009 | Teshima | H01J 37/28 700/121 |
| 7,485,858 B1 * | 2/2009 | Obara | H01J 37/222 250/306 |
| 7,777,183 B2 * | 8/2010 | Kaneoka | G01N 23/225 250/306 |
| 7,904,845 B2 | 3/2011 | Fouquet et al. | |
| 8,222,618 B2 | 7/2012 | Tokuda et al. | |
| 8,249,828 B2 | 8/2012 | Teshima et al. | |
| 8,309,919 B2 * | 11/2012 | Obara | H01J 37/222 250/306 |
| 8,341,518 B2 | 12/2012 | Hirai | |
| 8,357,894 B2 | 1/2013 | Toth et al. | |
| 8,421,007 B2 | 4/2013 | Terauchi et al. | |
| 8,748,816 B2 | 6/2014 | Kooijman et al. | |
| 8,765,496 B2 | 7/2014 | Nasser-Ghodsi et al. | |
| 2002/0072162 A1 | 6/2002 | Dor et al. | |
| 2003/0118149 A1 * | 6/2003 | Okuda | G01N 23/225 378/58 |
| 2004/0126909 A1 * | 7/2004 | Obara | G06T 7/0004 438/14 |
| 2005/0006583 A1 * | 1/2005 | Nozoe | G01N 23/20 250/311 |
| 2005/0121612 A1 * | 6/2005 | Okuda | G06T 7/0004 250/311 |
| 2006/0140340 A1 | 6/2006 | Kravis | |
| 2008/0100831 A1 * | 5/2008 | Patterson | G01N 21/93 356/237.4 |
| 2009/0206259 A1 * | 8/2009 | Obara | H01J 37/21 250/311 |
| 2010/0081217 A1 * | 4/2010 | Nagano | H01J 37/265 438/5 |
| 2011/0064191 A1 | 3/2011 | Toth et al. | |
| 2012/0292508 A1 | 11/2012 | Terauchi et al. | |
| 2013/0043130 A1 * | 2/2013 | Lednev | G01N 21/65 204/451 |
| 2013/0126728 A1 | 5/2013 | Waiblinger et al. | |
| 2013/0134308 A1 | 5/2013 | Endo et al. | |
| 2014/0084159 A1 * | 3/2014 | Yaeshima | H01L 22/12 250/310 |
| 2014/0131575 A1 | 5/2014 | Uemoto et al. | |
| 2015/0270094 A1 | 9/2015 | Ikku et al. | |
| 2015/0348751 A1 * | 12/2015 | Brogden | H01J 37/26 250/307 |
| 2016/0116425 A1 * | 4/2016 | Sinha | G01N 23/2252 250/307 |

OTHER PUBLICATIONS

Hideo Ota, et al."Scanning Surface Inspection System with Defect-review SEM and Analysis System Solutions", 2006, pp. 78-82, Hitachi Review, vol. 55, No. 2.

Hideo Ota, et al. "Scanning Surface Inspection System with Defect-review SEM and Analysis System Solutions", 2006, pp. 78-82, Hitachi Review vol. 55, No. 2., retrieved from the internet: http://www.hitachi.com/rev/pdf/2006/r2006_02_106.pdf.

Baltzinger Jean-Luc, et al. "Contamination monitoring and analysis in semiconductor manufacturing", published online on Apr. 1, 2010, 23 pages, retrieved from the internet: http://cdn.intechopen.com/pdfs-wm/9778.pdf.

SEM-based methodology for root cause analysis of wafer edge and bevel defects, Abstract, 2008 IEEE/SEMI Advanced Semiconductor Manufacturing Conference, 3 sheets [retrieved on Mar. 14, 2017], retrieved from the internet: http://ieeexplore.ieee.org/stamp/stamp.jsp?arnumber=4528998.

Al—Cu Pattern Wafer Study on Metal Corrosion Due to Chloride Ion Contaminants, Abstract, 2010 IEEE Transactions on Semiconductor Manufacturing, vol. 23, No. 4, 3 sheets [retrieved on Mar. 14, 2017], retrieved from the internet: http://ieeexplore.ieee.org/document/5545412/.

\* cited by examiner

AUTOMATED DECISION-BASED ENERGY-DISPERSIVE X-RAY METHODOLOGY AND APPARATUS

CROSS-REFERENCE TO RELATED APPLICATIONS

The present patent application claims the benefit of U.S. provisional patent application No. 62/069,048 filed Oct. 27, 2014, the disclosure of which is hereby incorporated by reference in its entirety. The present patent application also claims the benefit of U.S. provisional patent application No. 62/159,180 filed May 8, 2015, the disclosure of which is hereby incorporated by reference in its entirety. The present patent application also claims the benefit of U.S. provisional patent application No. 62/171,698 filed Jun. 5, 2015, the disclosure of which is hereby incorporated by reference in its entirety. The present patent application also claims the benefit of U.S. provisional patent application No. 62/204,325 filed Aug. 12, 2015, the disclosure of which is hereby incorporated by reference in its entirety. The present patent application claims priority to Indian patent application number 3080/CHE/2015, filed Jun. 19, 2015, the disclosure of which is hereby incorporated by reference in its entirety.

BACKGROUND OF THE INVENTION

Field of the Invention

The present disclosure relates to methods and apparatus for automated inspection and review of manufactured substrates, such as semiconductor wafers, using energy-dispersive x-ray spectroscopy.

Description of the Background Art

In a conventional scanning electron microscope (SEM) based inspection instrument, a manufactured substrate (such as a silicon wafer or a reticle) is scanned with a focused beam of electrons which results in the emission of secondary electrons from the substrate surface. The emitted electrons are detected, and the detection data is typically converted into images of the surface of the specimen. These images are then analyzed numerically to detect abnormalities (referred to as defects) in the manufactured substrate. The detected defects may be subsequently reviewed by further imaging.

The detected defects may also be classified, either manually or automatically, into different classes or categories. The classification of a defect may be used to determine its cause such that appropriate adjustments may be made in the manufacturing process so as to improve its yield.

In addition to producing secondary electrons, an electron beam striking a sample in an SEM also produces x-rays that are characteristic of the material of the sample. In energy-dispersive x-ray (EDX) spectroscopy, a solid state detector is positioned relatively close to the sample to collect x-rays emanating from the sample due to impingement by the electron beam. The detector receives and detects x-rays of different energies so as to obtain an energy spectrum of the detected x-rays. The energy spectrum provides information as to the elemental composition of the material being irradiated with electrons.

SUMMARY

One embodiment relates to a method for automated review of defects detected in a defective die on the target substrate. The method includes: obtaining a results file that includes locations of the defects; performing an automated review of the defects using an secondary electron microscope (SEM) so as to obtain electron-beam images of the defects; performing an automated classification of the defects into types based on morphology of the defects as determined from the electron-beam images; selecting defects of a specific type for automated energy-dispersive x-ray (EDX) review; and performing the automated EDX review on the defects of the specific type.

Another embodiment relates to an apparatus for automated review of defects detected on a target substrate. The apparatus includes: an electron beam column for generating a primary electron beam and focusing the primary electron beam onto a surface of the target substrate; a moveable stage for holding the target substrate under the primary electron beam; a deflector for deflecting the primary electron beam; an electron detector for detecting secondary electrons emitted from the surface of the target substrate due to impingement by the primary electron beam; an x-ray detector configured to detect x-rays emitted from the surface of the target substrate due to impingement by the primary electron beam; and a control system comprising non-transient data storage for storing computer-readable code and data and further comprising a processor for executing the computer-readable code. The computer-readable code comprises instructions to: obtain a results file that includes locations of the defects detected in a defective die on the target substrate; perform an automated secondary electron microscope (SEM) review of the defects so as to obtain electron-beam images of the defects; perform an automated classification of the defects into types based on morphology of the defects as determined from the electron-beam images; select defects of a specific type for automated energy-dispersive x-ray (EDX) review; and perform the automated EDX review on the defects of the specific type.

Another embodiment relates to a method of automated energy-dispersive x-ray (EDX) review of defects on a defective die. The method is automated under control of computer-readable instructions and includes: moving to a defect site; obtaining an EDX spectrum from the defect site; moving from the defect site to a reference site; obtaining the EDX spectrum from the reference site; and generating a difference spectrum from the EDX spectrum from the defect site and the EDX spectrum from the reference site.

In another embodiment, the method of automated energy-dispersive x-ray (EDX) review of defects on a defective die is performed on defects indicated to be in an array of repeated cells. In this case, the moving from the defect site to the reference site is performed by deflecting a primary electron beam by a cell dimension in one direction so that the reference site is at a location corresponding to the defect site in an adjacent cell.

In another embodiment, the method of automated energy-dispersive x-ray (EDX) review of defects on a defective die is performed on defects indicated to be in a non-array patterned structure. In this case, moving from the defect site to the reference site is performed by translation of a stage holding the target substrate so as to move a field of view of a scanning electron microscope from the defect site on the defective die to the reference site on the adjacent die.

Other embodiments, aspects and features are also disclosed.

DETAILED DESCRIPTION

Figure 1:
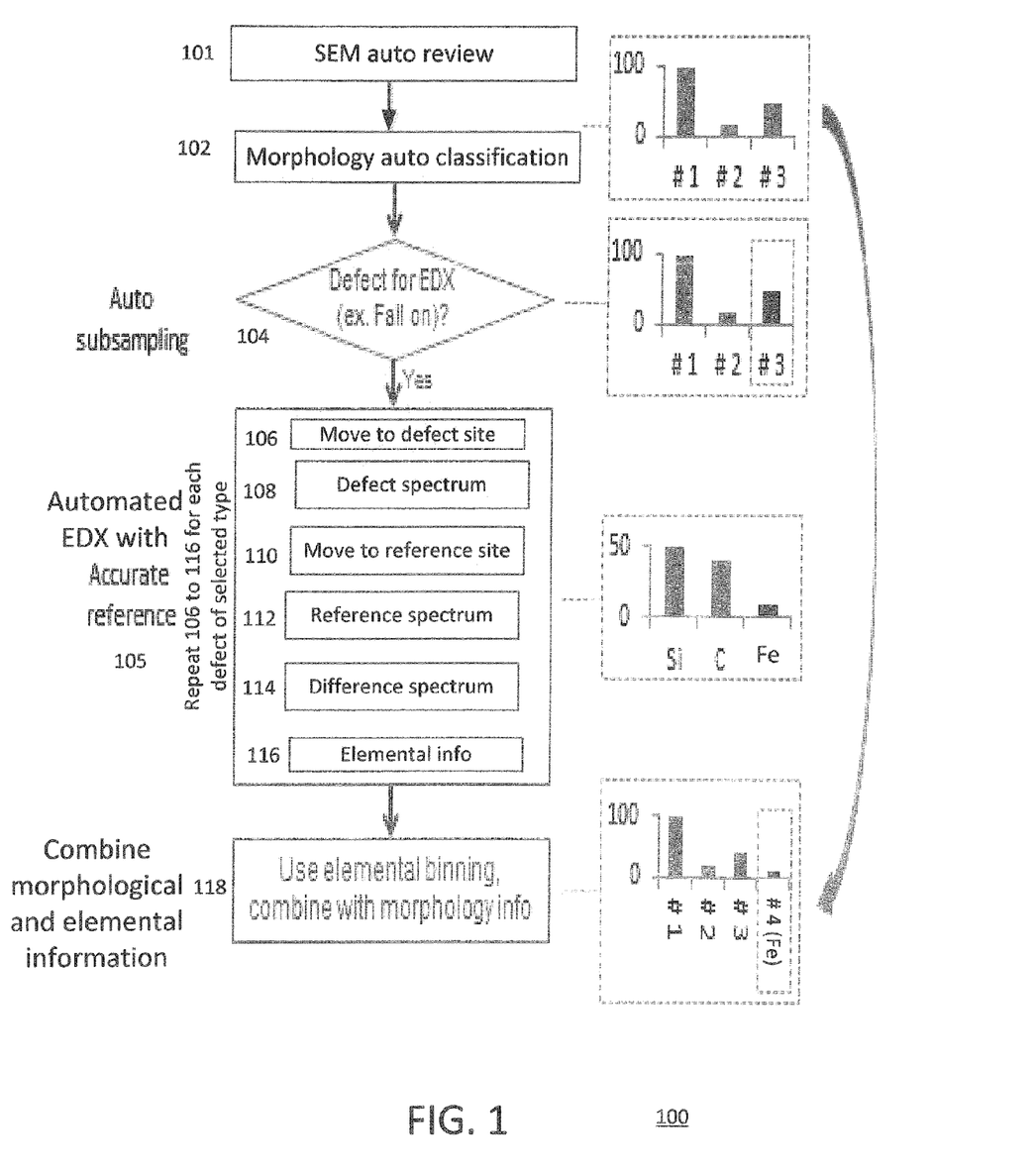
FIG. 1 is a flow chart of an automated decision-based EDX methodology in accordance with an embodiment of the invention.

FIG. 1 is a flow chart of an automated decision-based EDX method 100 in accordance with an embodiment of the invention. This method 100 may be performed after defect locations are identified by automated inspection. Such automated inspection may be performed by a same or a separate SEM apparatus, for example. The target substrate being inspected may be, for example, a silicon wafer having multiple dies formed thereon. Alternatively, the target substrate may be a reticle.

Referring to step 101, SEM automated review of identified defects may be performed. The SEM automated review may involve high-resolution SEM imaging of defects identified in a results file from the automated inspection.

Referring to step 102, after SEM automated review, morphology-based automatic classification may be performed. As depicted in the example bar graph on the right of step 102, the defects may be classified into defect types. The bar graph shows defect frequency vs. defect type. Three types (#1, #2, and #3) are depicted, but the number of types may be any number, of course. For example, a first defect type may be a hole, a second defect type may be a scratch, and a third defect type may be a particle. These are just a few example defect types. Other and different defect types may be, of course, utilized. For example, instead of having a particle defect type, there may be a large particle defect type and a small particle defect type, depending on the size of the particle, or there may be a round particle defect type and a non-round particle defect type, depending on the shape of the particle.

Referring to step 104, a selection is made of one (or more) types of defects for automated EDX review. The selection of the defect type for automated EDX review may be pre-programmed or pre-configured so as to be automatically performed by the executable program code performing the automated decision-based EDX method 100. As depicted in the example bar graph on the right of step 104, the selected type may be type #3. For example, type #3 may correspond to a defect type associated with particles, which may also be referred to as "fall on" defects. This automated selection of the defect type for automated EDX review per step 104 may be referred to herein as automated (auto) subsampling. Further description of auto subsampling is provided below in relation to FIG. 2.

After the auto subsampling of step 104, an automated EDX review 105 with accurate reference data may be performed on the defects of the selected type. To obtain accurate reference data, the automated EDX review 105 may involve repeating steps 106 to 116 for each defect of the selected type.

Referring to step 106, movement may be performed to a defect site. The movement to the defect site may be accomplished by translating the stage such that the defect site is within the field of view of the SEM. This may be performed based on the location coordinates of the defect site obtained from the stored results of the SEM automated review.

Referring to step 108, an EDX spectrum (the defect spectrum) is obtained from the defect site. This may involve translating the substrate so that the defect site is in the field of view of the SEM and scanning the primary electron beam over the defect site while detecting the energy spectrum of x-rays thereby generated. The defect spectrum from each defect site may be stored in a manner so as to be associated with the location of (coordinates for) the defect site.

Referring to step 110, movement may be performed from the defect site to a reference site aligned in correspondence to the defect site. As described further below in relation to FIG. 3, if the defect site is indicated to be in an array of repeating cells, then the movement to the reference site may be accomplished by deflecting the primary electron beam to a corresponding location in an adjacent cell. As described further below in relation to FIG. 5, if the defect site is indicated to be in a non-array patterned structure (i.e. the patterned structure is not an array of repeating cells), then the movement to the reference site may be accomplished by translating the stage to a corresponding location on an adjacent die on the target substrate. The indication of whether or not the defect site is in an array or non-array patterned structure may be provided by data in the results file.

Referring to step 112, an EDX spectrum (the reference spectrum) is obtained from the reference site. This may involve scanning the primary electron beam over the reference site while detecting the energy spectrum of x-rays thereby generated. The reference spectrum may be stored in a manner so as to be associated with the corresponding defect site.

Referring to step 114, a difference spectrum may be generated. In one implementation, normalization of the defect spectrum and a corresponding reference spectrum may be performed, and the normalized reference spectrum may be subtracted from the normalized defect spectrum to obtain the difference spectrum.

Referring to step 116, elemental information for the defect may be obtained from the difference spectrum. For example, if the selected defect type is a particle type, then the elemental information may indicate the elemental composition of the particle. Advantageously, the elemental information obtained using the methodology disclosed herein is more accurate than that obtained from a conventional automated EDX review procedure. This is because the methodology disclosed herein more accurately locates the reference site compared with previous methods.

An example bar graph is provided on the right of steps 106 to 116. As seen in the example bar graph, the elemental information for the particle defects may indicate that the particle defects have an elemental composition that is either primarily silicon (Si), or primarily carbon (C), or primarily iron (Fe).

Referring to step 118, the more accurate elemental information obtained using the presently-disclosed methodology may be combined with the morphological information from step 102. An example bar graph with the combined information is provided on the right of step 118. The bar graph shows defect frequency vs. defect type. As shown in the example bar graph, four types of defect bins are depicted. The first two types (#1 and #2) correspond to the morphological-based types (hole and scratch, respectively) discussed above in relation to step 102. In this case, the third type (#3) and fourth type (#4) may both be for particles, depending on their elemental composition. For example, the fourth type (#4) may correspond to particles that are primarily (Fe) in composition, while the third type (#3) may correspond to particles of other composition (i.e. not Fe). Note that this example is provided for illustrative purposes. Other defect types may be provided that have different combinations of morphological and elemental information.

Figure 2:
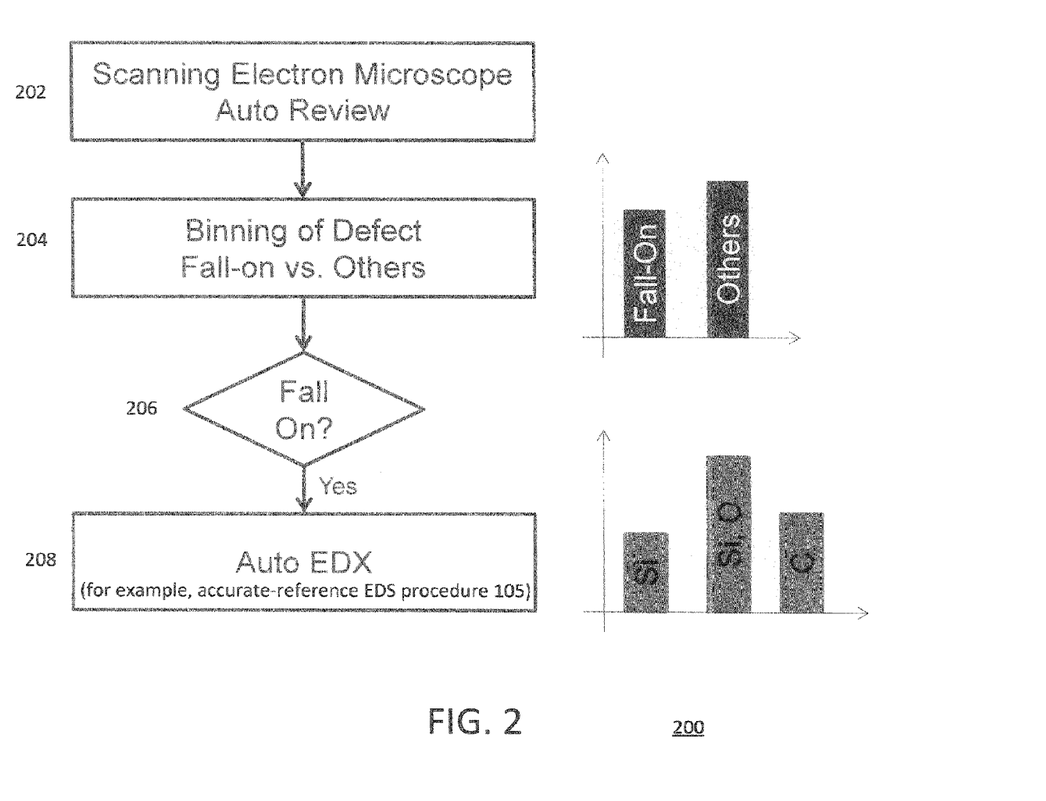
FIG. 2 is a flow chart of a process flow for automated subsampling of identified defects in accordance with an embodiment of the invention.

FIG. 2 is a flow chart of a process flow 200 for automated subsampling of identified defects in accordance with an embodiment of the invention. The automated subsampling advantageously reduces the number of defects to which the EDX review is applied and, hence, reduces the time needed to perform the automated EDX review. This is because the EDX review is applied only to a selected type (or selected types) of defects, rather than all defects identified in a results file from the automated inspection.

Referring to step 202, SEM automated review of identified defects may be performed. The SEM automated review may involve high-resolution SEM imaging of defects identified in a results file from the automated inspection.

Referring to step 204, the defects may be classified (i.e. "binned") into defect types. In this instance, as shown in bar graph on the right of step 204, the defects may be classified into a "fall on" (particle) defect type and an "others" (non-particle) defect type.

Referring to step 206, a selection is made of only defects of the "fall on" defect type for EDX review. In other words, the auto subsampling selects only fall-on defects for EDX review, while EDX review is not performed on other defects.

Referring to step 208, EDX review is performed in an automated manner on the selected defects. In accordance with an embodiment of the invention, the automated EDX review may be performed with accurate reference spectra using the automated EDX procedure 105 with accurate reference spectra described above in relation to FIG. 1. For example, as shown in bar graph on the right of step 208, the fall-on defects may be categorized (binned) into a silicon (Si) particle type, a silicon oxide (Si, O) particle type, and a carbon (C) particle type.

Figure 3:
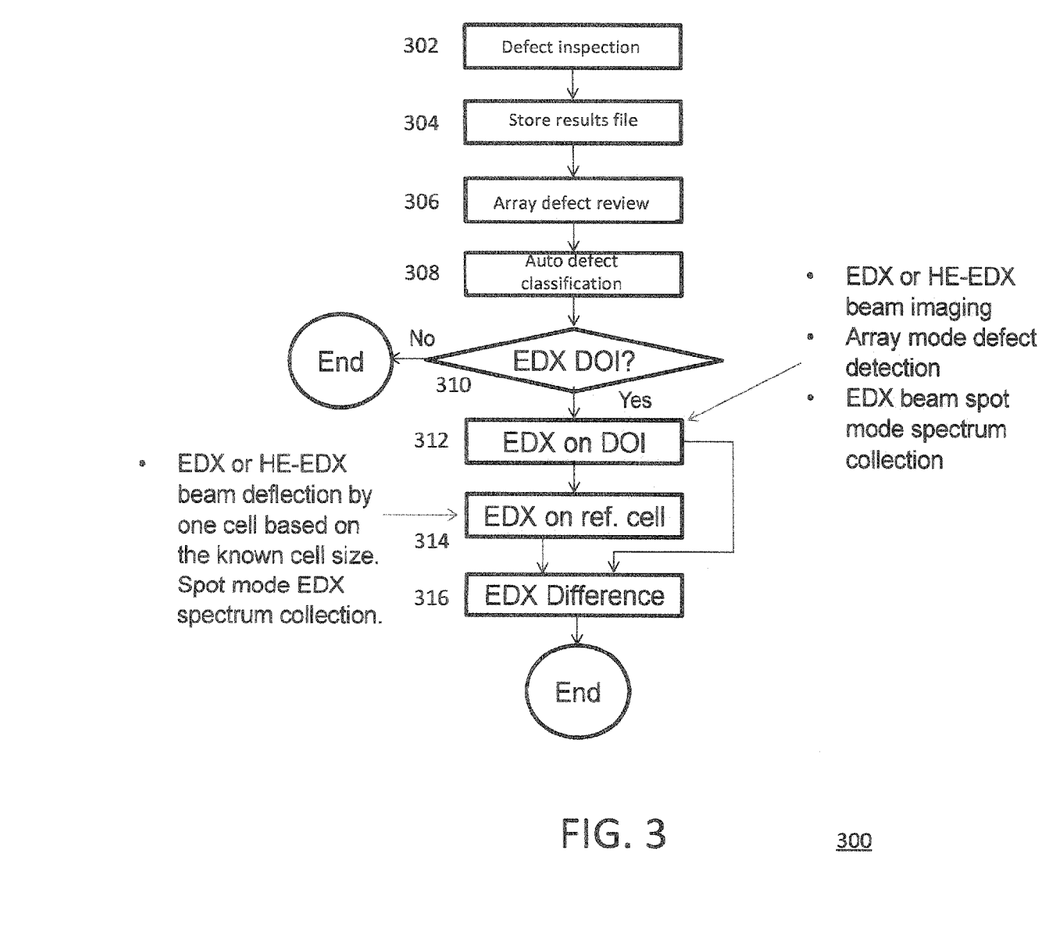
FIG. 3 is a flow chart of a process flow for automated EDX review in an array mode in accordance with an embodiment of the invention.

FIG. 3 is a flow chart of a process flow for automated EDX review in an array mode in accordance with an embodiment of the invention. The array mode may be used for regions on the target substrate that are patterned with an array of repeated cells. For example, the target substrate may include an array of memory cells, and the array mode may be used for automated EDX review in the interior of the array of memory cells.

Referring to step 302, automated inspection may be performed to detect defects in the target substrate. The automated inspection may be performed, for example, using an SEM-based automated inspection apparatus. The inspection tool may be integrated with, or separate from, the SEM-based automated review apparatus.

Referring to step 304, data regarding the defects detected by the automated inspection may be stored in a results file. The information includes coordinate data as to the locations of the defects.

Referring to step 306, an SEM automated review of the detected defects in the array may be performed. The SEM automated review may involve, among other steps, high-resolution SEM imaging of the defects identified in the results file from the automated inspection.

Referring to step 308, the defects may be classified (i.e. "binned") into defect types. This classification may be made based on the morphology of the defects, as observable from the high-resolution SEM imaging. For example, the defect types may include a hole type, a scratch type, and a particle ("fall on") type. These are just a few example defect types. Other and different defect types may be, of course, utilized.

Referring to step 310, this step may be performed for each defect in the results file. In this step, a defect in the results file may be selected as the defect of interest (DOI), and a determination may be made as to whether or not EDX review is to be applied to the DOI. This determination may be made in an automated manner based on the defect type of the DOI. If EDX review is not to be applied to the DOI, then the processing of the present DOI may end, and the method 300 may loop back and perform step 310 for a next defect selected to be the DOI, if any. On the other hand, if EDX review is to be applied to the DOI, then the method 300 may go forward to perform steps 312 to 316.

Regarding step 312, EDX is applied to the DOI. This may involve translating the stage to move the site of the DOI to be within the field of view and obtaining an EDX spectrum from the DOI.

Regarding step 314, EDX is applied to the corresponding site in a reference cell. This may involve deflecting the primary electron beam in one direction by a distance that is equal to a cell dimension in that direction. This deflection moves the primary electron beam so that it impinges upon a location (the reference spot) in an adjacent cell (the reference cell) which corresponds to the location of the DOI in its cell. An EDX spectrum may then be obtained from the reference spot.

Regarding step 316, a difference spectrum between the EDX spectrum of the DOI and the EDX spectrum of the reference spot may be generated. The EDX spectra may be normalized before generating the difference spectrum. Thereafter, the difference spectrum may be used to obtain elemental information about the DOI, as described above in relation to step 116 in FIG. 1.

Figure 4:
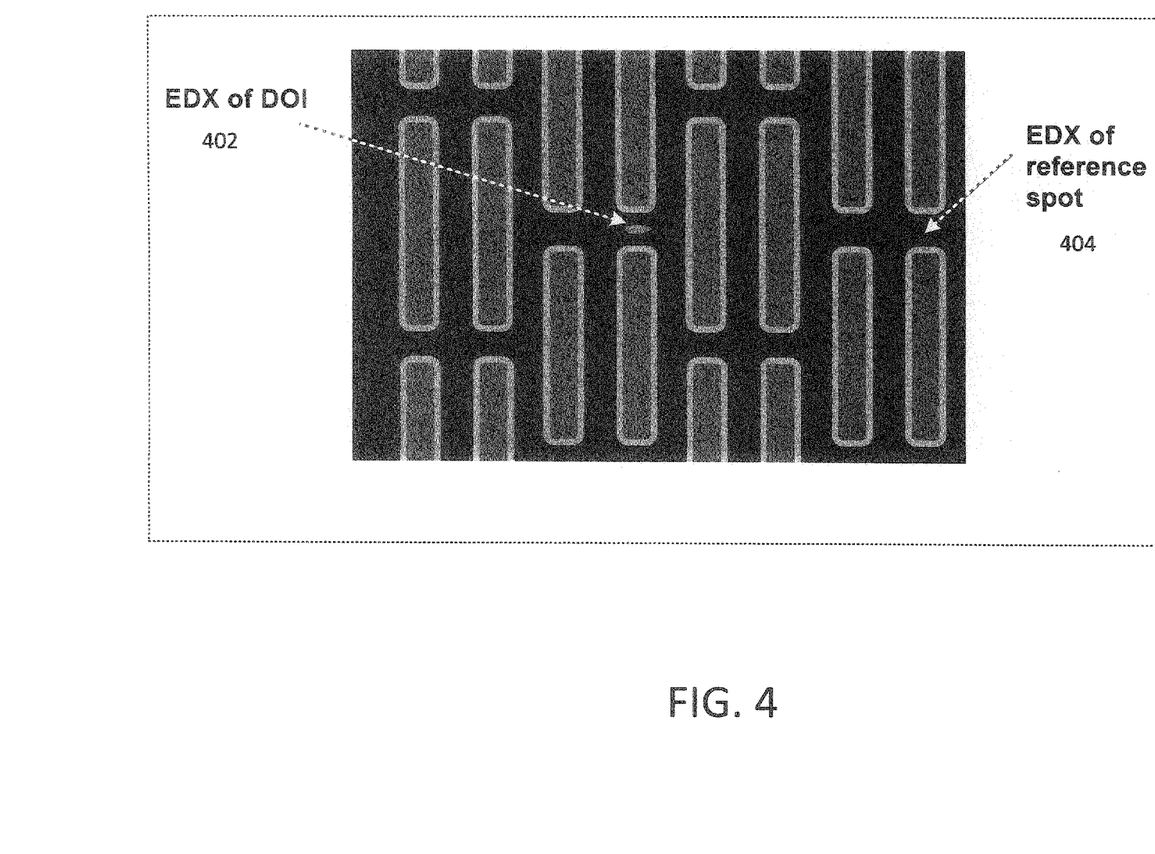
FIG. 4 shows an electron micrograph depicting a defect of interest (DOI) and a corresponding reference spot in a neighboring cell in accordance with an embodiment of the invention.

FIG. 4 shows an electron micrograph depicting a defect of interest (DOI) 402 and a corresponding reference spot 404 in a neighboring cell in accordance with an embodiment of, the invention. In this case, the DOI 402 is within an array of repeating cells. As such, the automated EDX may be performed in an array mode, where reference spectrum is obtained by deflecting the electron beam by a width (or height) of a cell in the array.

Figure 5:
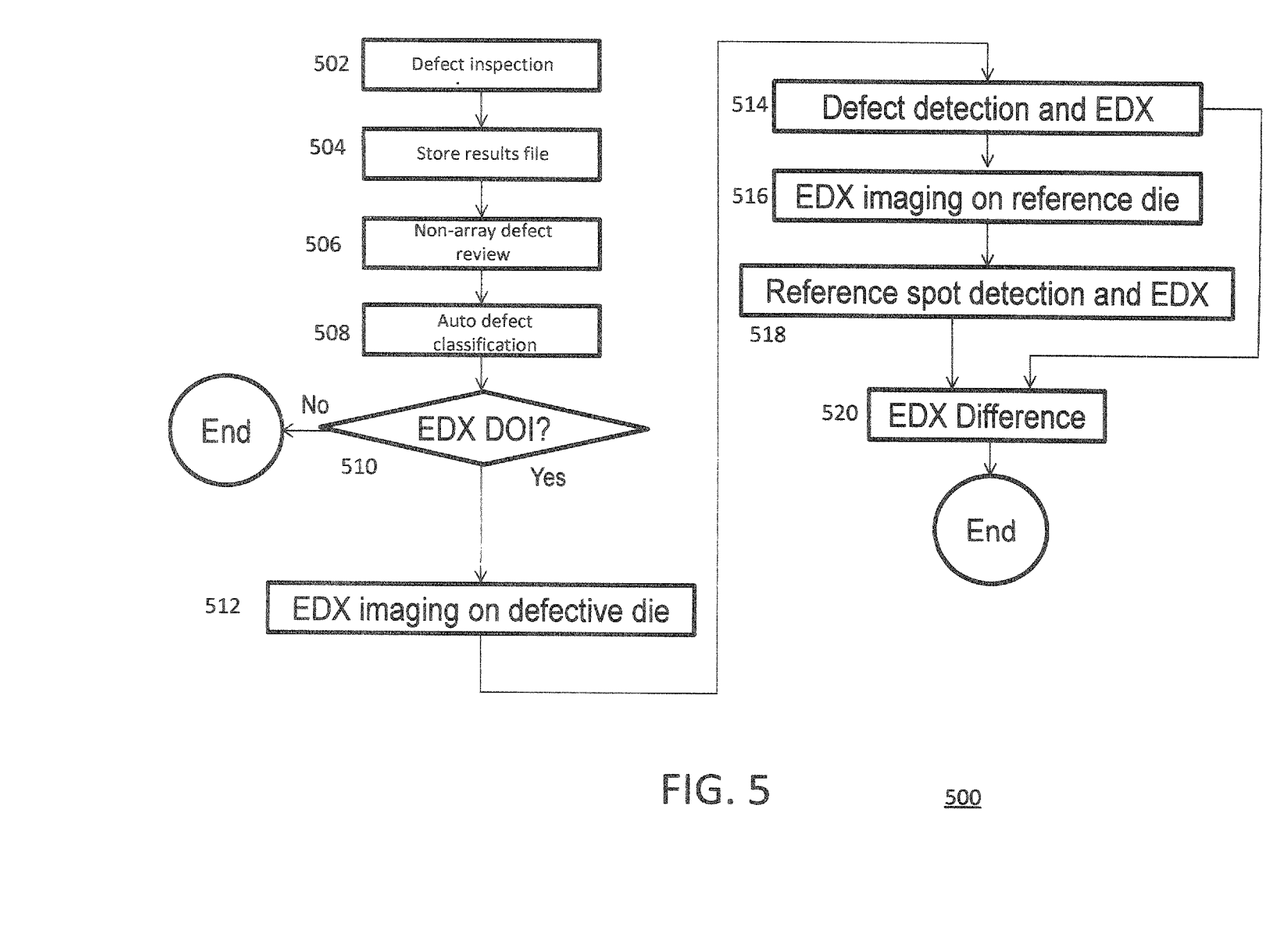
FIG. 5 is a flow chart of a process flow for automated EDX review in a non-array mode in accordance with an embodiment of the invention.

FIG. 5 is a flow chart of a process flow for automated EDX review in a non-array mode in accordance with an embodiment of the invention. The non-array ("random") mode may be used for regions of the target substrate which are not patterned with an array of repeating cells. For example, an application specific integrated circuit may include a region with customized logic circuitry, and the non-array mode may be used for automated EDX review within this region.

Referring to step 502, automated inspection may be performed to detect defects in the target substrate. The automated inspection may be performed, for example, using an SEM-based automated inspection apparatus. The inspection tool may be integrated with, or separate from, the SEM-based automated review apparatus.

Referring to step 504, data regarding the defects detected by the automated inspection may be stored in a results file. The information includes coordinate data as to the locations of the defects.

Referring to step 506, an SEM automated review of the detected defects may be performed. In this case, the defects may be in a region that is not an array of repeated cells (i.e. a non-array region) such that the automated review may be performed in a "random" (non-array) mode. The SEM automated review may involve, among other steps, high-resolution SEM imaging of the defects identified in the results file from the automated inspection.

Referring to step 508, the defects may be classified (i.e. "binned") into defect types. This classification may be made based on the morphology of the defects, as observable from the high-resolution SEM imaging. For example, the defect types may include a hole type, a scratch type, and a particle ("fall on") type. These are just a few example defect types. Other and different defect types may be, of course, utilized.

Referring to step 510, this step may be performed for each defect in the results file. In this step, a defect in the results file may be selected as the defect of interest (DOI), and a determination may be made as to whether or not EDX review is to be applied to the DOI. This determination may be made in an automated manner based on the defect type of the DOI. If EDX review is not to be applied to the DOI, then the processing of the present DOI may end, and the method 500 may loop back and perform step 510 for a next defect selected to be the DOI, if any. On the other hand, if EDX review is to be applied to the DOI, then the method 500 may go forward to perform steps 512 to 520.

Regarding step 512, the electron-beam imaging may be performed in a field of view centered at the defect location coordinates of the DOI on the defective die so as to image an area encompassing the defect site. Preferably, the image of the area surrounding the defect site may be a high-resolution image.

Regarding step 514, EDX is applied to the DOI so as to obtain an EDX spectrum for the DOI (the defect spectrum). The elemental information from this EDX spectrum includes not only elemental information from the DOI, but also elemental information from material surrounding the DOI.

Regarding step 516, the electron-beam imaging may be performed in a field of view centered at the defect location coordinates on the reference die (instead of the defective die) so as to image an area encompassing the reference site. Preferably, the image of the area surrounding the reference site may be a high-resolution image.

After step 514 and before step 516, the stage holding the target substrate is translated to move from the defect site on the defective die to the reference site on the reference die (which is preferably adjacent to the defective die). Furthermore, the pattern of the image encompassing the reference site may be aligned to the pattern of the image encompassing the defect site, and the aligned images may be used to determine with high accuracy the location of the reference site.

Regarding step 518, EDX is applied to the reference site so as to obtain an EDX spectrum from the reference spot (the reference spectrum). After normalization, this reference spectrum that may be subtracted from the defect spectrum to obtain a difference spectrum, as indicated in step 520. Thereafter, the difference spectrum may be used to obtain elemental information about the DOI, as described above in relation to step 116 in FIG. 1.

Figure 6:
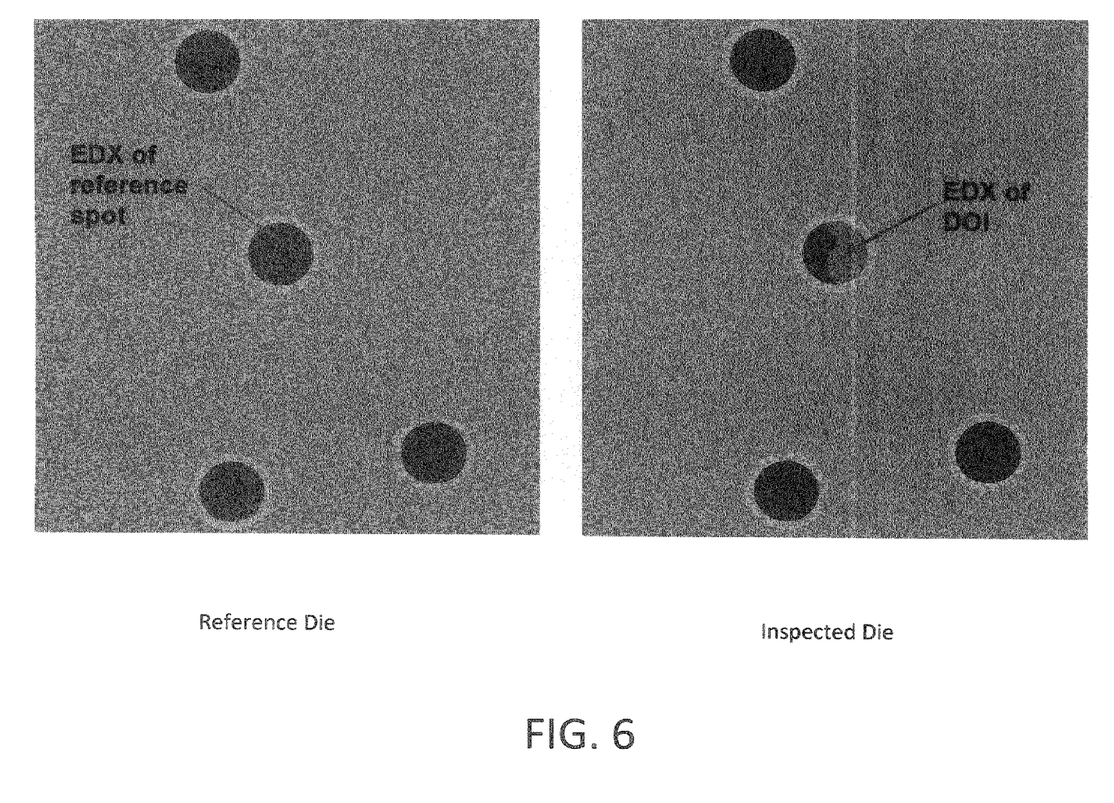
FIG. 6 shows electron micrographs depicting a defect of interest (DOI) and a corresponding reference spot on a reference die in accordance with an embodiment of the invention.

FIG. 6 shows electron micrographs depicting a defect of interest (DOI) and a corresponding reference spot on a reference die in accordance with an embodiment of the invention. In this case, the DOI is within a non-array portion of the die. As such, the automated EDX may be performed in a non-array mode, where reference spectrum is obtained by first locating the reference spot on the reference die, and stage translation is used to move between the DOI and the reference spot.

Figure 7:
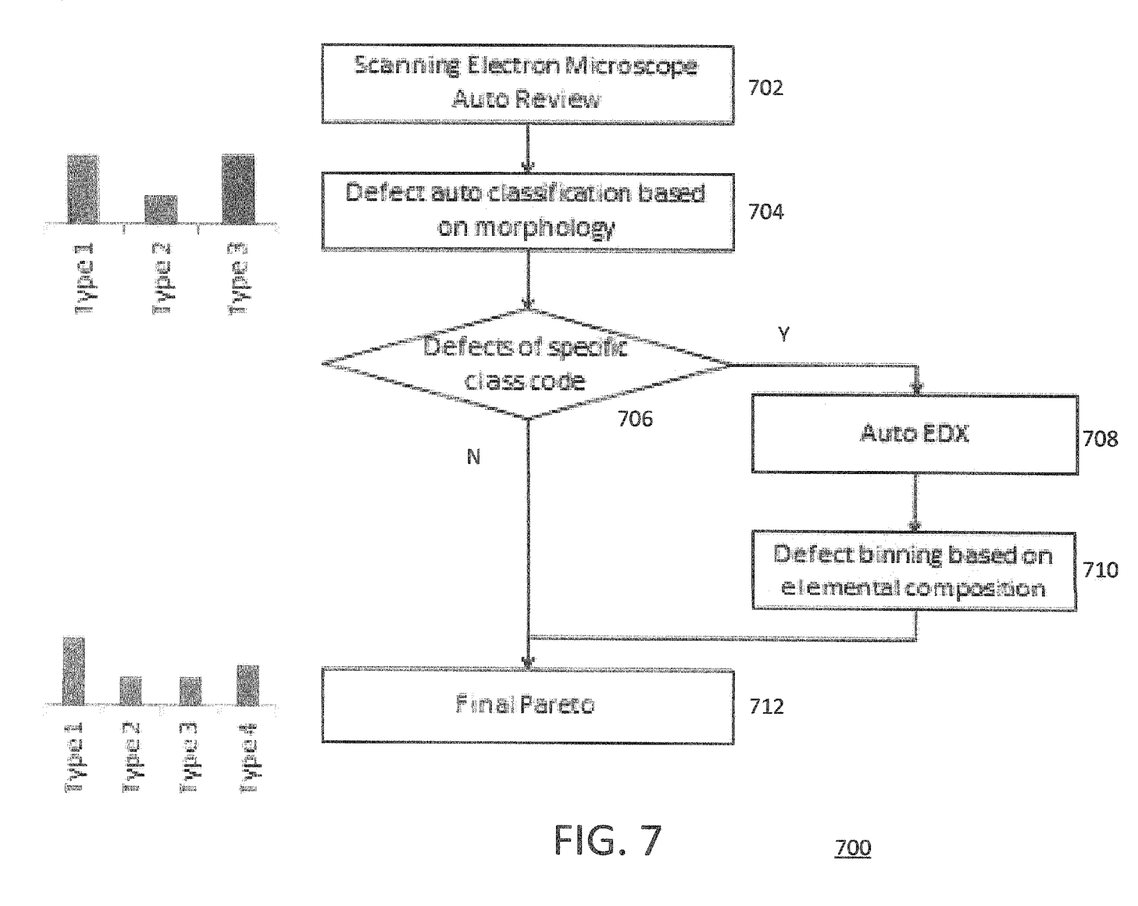
FIG. 7 is a flow chart of an automated process for combining morphological defect results with elemental defect results to obtain a final pareto in accordance with an embodiment of the invention.

FIG. 7 is a flow chart of an automated process for combining morphological defect results with elemental defect results to obtain a final pareto in accordance with an embodiment of the invention.

Referring to step 702, an SEM automated review of detected defects may be performed. The SEM automated review may involve, among other steps, high-resolution SEM imaging of the defects identified in a results file from the automated inspection.

Referring to step 704, automated classification of the defects may be performed based on the morphology of the defects. The defects may be classified (i.e. "binned") into defect types, and each defect type may be represented by a class code. For example, the defect types may include a hole type as Type 1, a scratch type as Type 2, and a particle ("fall on") type as Type 3. These are just a few example defect types. Other and different defect types may be, of course, utilized.

Referring to step 706, defects of a specific class code may be selected for automated EDX review, while the automated EDX review may be skipped for defects of other class codes. In other words, for each defect, a determination may be made as to whether or not the defect is of the specific class code. If the class code is not the specific class code, then no automated EDX review of the present defect is performed, and the method 700 may loop back and perform step 706 for a next defect, if any. On the other hand, if the class code is the specific class code, then the method 700 may go forward to perform steps 708 and 710.

Referring to step 708, for defects of the specific class code, the automated EDX review is performed. To provide an accurate reference spectrum, the automated EDX review may be performed with the steps 312 to 316 described above in relation to FIG. 3 if the defect being reviewed is within an array of repeated cells, or with the steps 512 to 520 if the defect being reviewed is not within such an array region. As a result of step 708, a difference spectrum may be obtained for each defect of the specific class code.

Referring to step 710, the difference spectrum may be used to obtain an elemental composition for each defect of the specific class code, and defects of the specific class code may be binned based on their elemental composition. For example, if the specific class code corresponds to particle or "fall on" defects, then these defects may be separated into several elemental-composition bins based on their elemental composition. For example, the elemental-composition bins may include a silicon (Si) bin, a silicon oxide (Si, O) bin, and a carbon (C) bin.

Referring to step 712, a defect Pareto (Final Pareto) may be generated that uses and combines both morphological and elemental information in categorizing the defects. A defect Pareto is a bar graph of defect frequency by type. The defect Pareto may be used to make decisions about what corrective action needs to be taken to reduce defectivity. In one implementation, the defects that have the specific class code may be divided based on the elemental composition of the defects.

For example, consider that the morphological defect types from step 704 includes a hole type as Type 1, a scratch type as Type 2, and a particle ("fall on") type as Type 3. Consider further that the specific class code used to select defects for automated EDX review in step 706 is the class code for Type 3 (particle or "fall on" defects). Consider further that these fall-on defects may be divided based on the elemental composition of the particles. For example, fall-on defects that are silicon oxide may be coded as Type 4, while fall-on defects that are of other compositions (for example, Si or C) may remain coded as Type 3. The resultant bar graph to the left of step 712 depicts the Final Pareto in this example.

Figure 8:
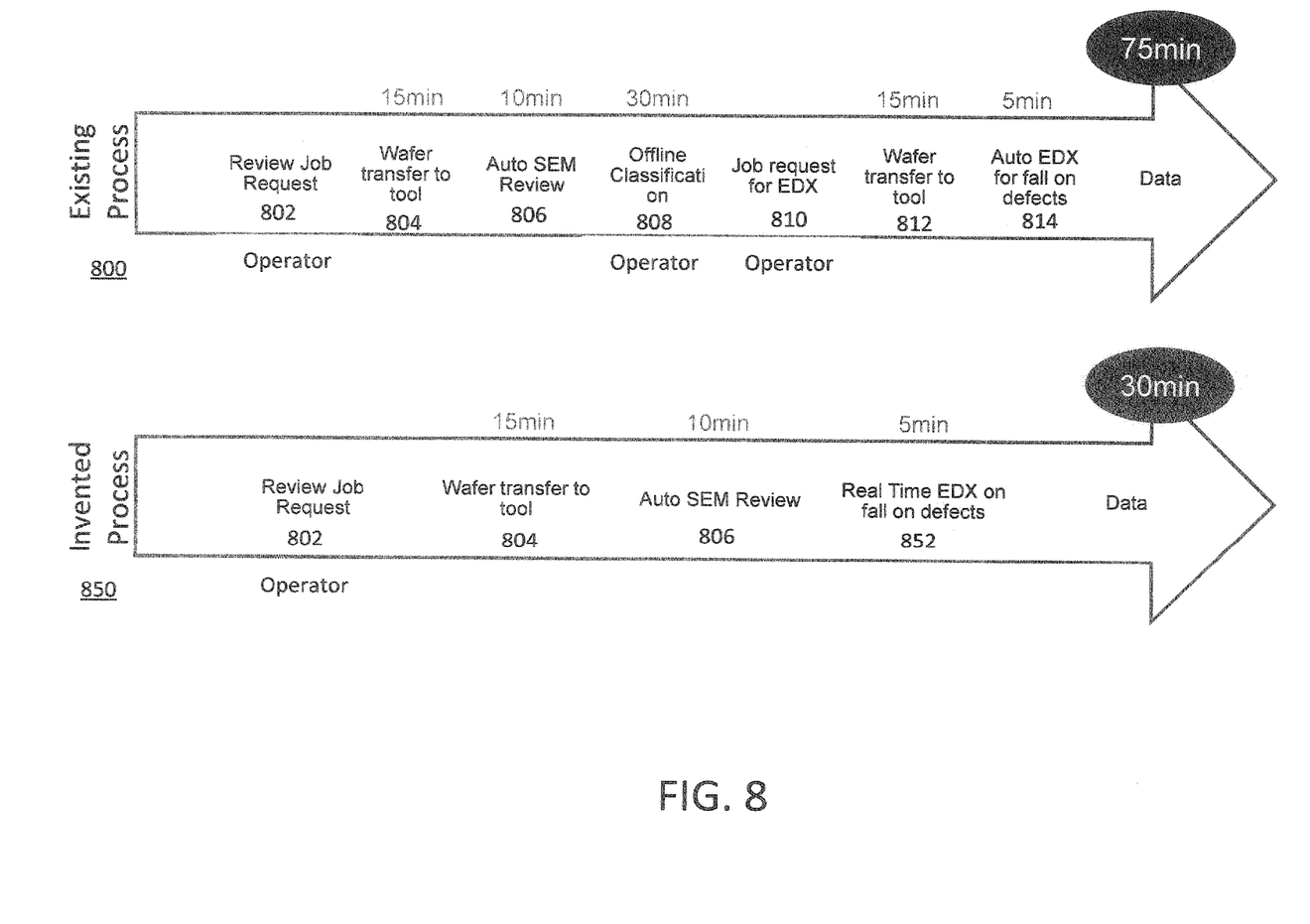
FIG. 8 is a diagram comparing an existing process for automated EDX review with an invented process for automated EDX review in accordance with an embodiment of the invention.

FIG. 8 is a diagram comparing an existing process 800 for automated EDX review with an invented process 850 for automated EDX review in accordance with an embodiment of the invention. As depicted, the invented process 850 advantageously requires fewer steps and provides results more rapidly than the existing process 800.

The existing process 800 includes the following steps: a review job requested 802 by the operator; the wafer to be reviewed by SEM is transferred 804 to the review tool (which may take roughly 15 minutes); automated SEM review is performed 806 (which may take roughly 10 minutes); offline classification of defects into defect types is performed 808 by the operator (which may take roughly 30 minutes); an EDX job is requested 810 by the operator for a set of defects classified under a selected type (for example, fall-on defects); the wafer to be reviewed by EDX is transferred 812 to the EDX tool (which may take roughly 15 minutes); and automated EDX may then be performed 814 on the set of defects (which may take roughly 5 minutes).

As indicated, operator action is required for three steps (steps 802, 808 and 810) in the existing process 800. The existing process 850 may typically take about 75 minutes until the desired EDX data is obtained.

In contrast, the invented process 850 includes the following steps: a review job requested 802 by the operator; the wafer to be reviewed by SEM is transferred 804 to the review tool (which may take roughly 15 minutes); automated SEM review is performed 806 (which may take roughly 5 minutes); and real-time EDX review may then be performed 852 using the automated decision-based method 100 described above in a general manner in relation to FIG. 1 (see steps 102 through 118).

As indicated, operator action is required for only the first step (step 802) in the invented process 850 (rather than three steps in the existing process 800). Furthermore, the invented process 850 may typically take only about 30 minutes until the desired EDX data is obtained (rather than about 75 minutes using the existing process 800).

Figure 9:
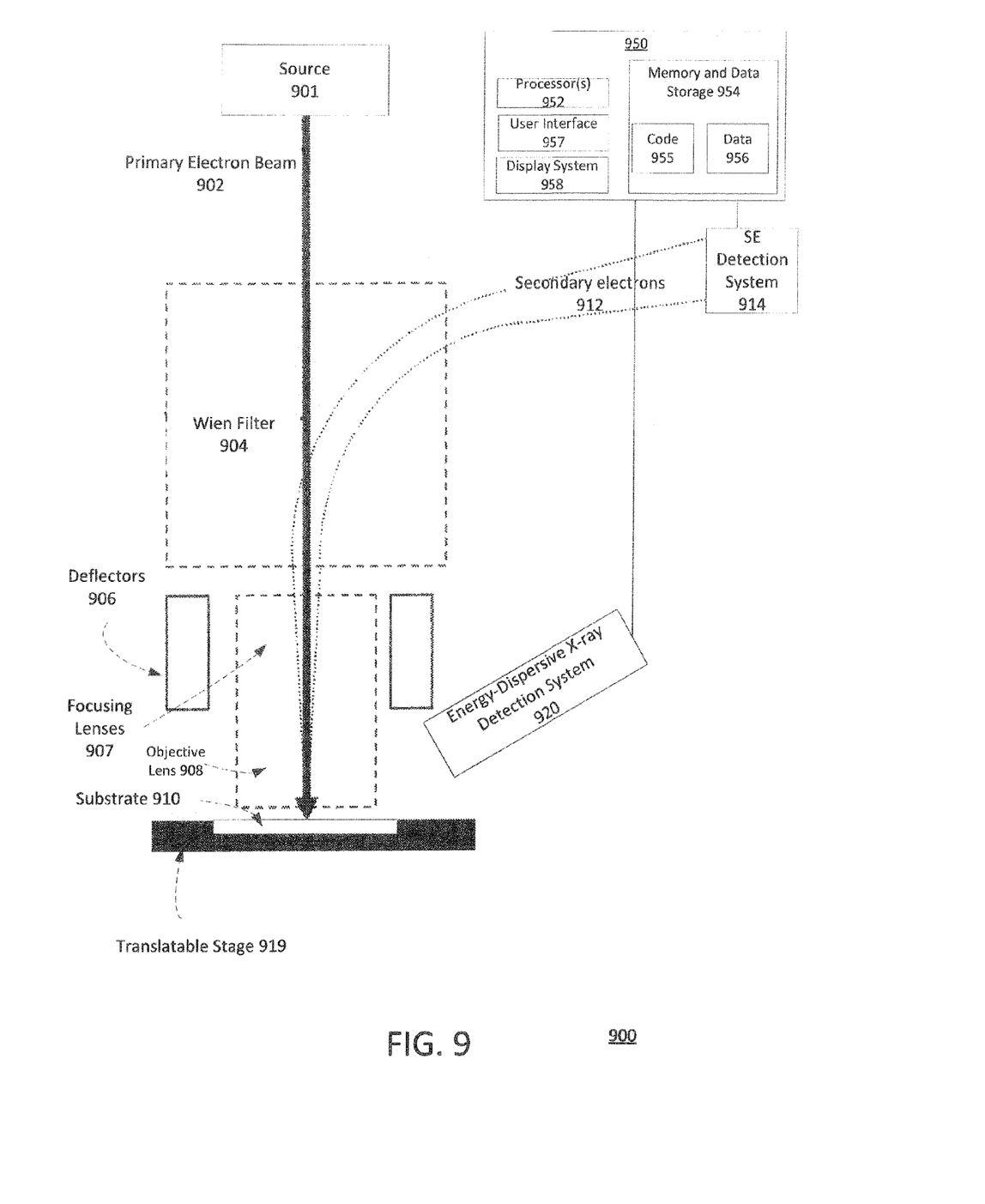
FIG. 9 is a schematic diagram of a scanning electron microscope apparatus with an energy-dispersive x-ray (EDX) detection system in accordance with an embodiment of the invention.

FIG. 9 is a schematic diagram of a scanning electron microscope apparatus 900 with an energy-dispersive x-ray (EDX) detection system 920 in accordance with an embodiment of the invention. As shown in the cross-sectional view of FIG. 9, the electron beam column may include a source 901, a Wien filter, scanning deflectors 906, focusing lenses 907, an objective lens 908, and a translatable stage 919 holding a target substrate 910.

The source 901 generates an incident electron beam (primary electron beam) 902. The incident electron beam 902 may pass through a Wien filter 904. The Wien filter 904 is an electron-optical element configured to generate electrical and magnetic fields which cross each other. Controllable electrostatic deflectors 906 and focusing electron lenses 907 may be utilized. The deflectors 906 may apply independently-controllable electrostatic fields in the x direction and in the y direction. The deflectors 906 may be controlled to scan the e-beam across the surface of the target substrate 910 or deflect the e-beam for other purposes. The target substrate 910 may be, for example, a patterned substrate, such as an integrated circuit being manufactured or a reticle for lithography.

The focusing electron lenses 907 are utilized to focus the incident electron beam 902 into a beam spot on the surface of the wafer or other substrate sample 910. In accordance with one embodiment, the focusing lenses 907 may operate by generating electric and/or magnetic fields.

As a result of the scanning of the incident electron beam 902, secondary electrons and x-rays are emitted or scattered from the surface of the target substrate 910 (which may be, for example, a semiconductor wafer or a reticle). The target substrate 910 may be held by a movable stage 911.

The secondary electrons may be extracted from the target substrate 910 by exposure to the electromagnetic field of the objective (final) lens 908. The electromagnetic field acts to confine the emitted electrons to within a relatively small distance from the incident electron beam optic axis and to accelerate these electrons up into the column. In this way, a secondary e-beam 912 is formed from the secondary electrons.

The Wien filter 904 deflects the secondary e-beam 912 from the optic axis of the incident electron beam 902 to a detection axis that is the optical axis for the secondary electron (SE) detection system 914 of the apparatus. This serves to separate the scattered e-beam 912 from the incident electron beam 902. The SE detection system 914 detects the secondary e-beam 912 and generates data signals that may be utilized to create images of the surface of the target substrate.

An instrument control and data processing (control/processing) system 950 may include one or more processors (i.e. microprocessors or microcontrollers) 952, data storage (including, for example, hard disk drive storage and memory chips) 954, a user interface 957 and a display system 958. The data storage 954 may store or hold computer-readable program code (instructions) 955 and data 956, and the processor 952 may execute the program code 955 and process the data 956. The user interface 957 may receive user inputs. The display system 958 may be configured to display image data and other information to a user.

The control/processing system 950 may be connected to, and may be used to control, various components of the e-beam column so as to implement methods or procedures disclosed herein. For example, the movement of the stage 911, and the scanning by the deflectors 906 may be controlled by computer-readable program code 955 executed by the control/processing system 950.

In addition, the control/processing system 950 may also process the electron image data from the SE detection system 914 and x-ray data from the EDX detection system 920. In particular, the computer-readable program code 955 in the control/processing system 950 may be used to implement procedures relating to the automated EDX methodology as described herein.

CONCLUSION

The above-described diagrams are not necessarily to scale and are intended be illustrative and not limiting to a particular implementation. Specific dimensions, geometries, and lens currents of the magnetic objective lens will vary and depend on each implementation.

The above-described technique may be used, for example, in an automatic inspection and defect analysis system and applied to the inspection and review of wafers, X-ray masks and similar substrates in a production environment. Other uses are also possible.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for automated review of defects detected in a defective die on the target substrate, the method comprising:
    obtaining a results file that includes locations of the defects;
    performing an automated review of the defects using an secondary electron microscope (SEM) so as to obtain electron-beam images of the defects;
    performing an automated classification of the defects into types based on morphology of the defects as determined from the electron-beam images;
    selecting defects of a specific type for automated energy-dispersive x-ray (EDX) review;
    performing the automated EDX review on the defects of the specific type; and
    generating a defect pareto that is a distribution of defect frequency by type, wherein the defect pareto combines morphological and elemental information by dividing defects of the specific type based on morphology of the defects into multiple types depending on elemental information.

2. The method of claim 1, wherein performing the automated EDX review comprises, for each defect of the specific type:
    movement to a defect site;
    obtaining an EDX spectrum from the defect site;
    movement from the defect site to a reference site;
    obtaining the EDX spectrum from the reference site; and
    generating a difference spectrum from the EDX spectrum from the defect site and the EDX spectrum from the reference site.

3. The method of claim 2, wherein the defect site is indicated to be in an array of repeating cells, and wherein the movement from the defect site to the reference site is performed by deflecting a primary electron beam by a cell dimension in one direction so that the reference site is at a location corresponding to the defect site in an adjacent cell.

4. The method of claim 2, wherein the defect site is indicated to be in a non-array patterned structure, further comprising:
    electron-beam imaging to obtain a first image of area encompassing the defect site on the defective die;
    electron-beam imaging to obtain a second image of an area encompassing the reference site on an adjacent die; and
    determining a location of the reference site in the second image after aligning the second image to the first image.

5. The method of claim 4, wherein the movement from the defect site to the reference site is performed by translation of a stage holding the target substrate so as to move a field of view of the SEM from the defect site on the defective die to the reference site on the adjacent die.

6. The method of claim 2, further comprising:
    deriving elemental information from the difference spectrum for each defect of the specific type.

7. The method of claim 1, wherein the defect pareto comprises a bar graph of defect frequency versus type.

8. An apparatus for automated review of defects detected on a target substrate, the apparatus comprising:
    an electron beam column for generating a primary electron beam and focusing the primary electron beam onto a surface of the target substrate;
    a moveable stage for holding the target substrate under the primary electron beam;
    a deflector for deflecting the primary electron beam;
    an electron detector for detecting secondary electrons emitted from the surface of the target substrate due to impingement by the primary electron beam;
    an x-ray detector configured to detect x-rays emitted from the surface of the target substrate due to impingement by the primary electron beam; and
    a control system comprising non-transient data storage for storing computer-readable code and data and further comprising a processor for executing the computer-readable code, wherein the computer-readable code comprises instructions to:
        obtain a results file that includes locations of the defects detected in a defective die on the target substrate;
        perform an automated secondary electron microscope (SEM) review of the defects so as to obtain electron-beam images of the defects;
        perform an automated classification of the defects into types based on morphology of the defects as determined from the electron-beam images;
        select defects of a specific type for automated energy-dispersive x-ray (EDX) review; and
        perform the automated EDX review on the defects of the specific type; and
        generating a defect pareto that is a distribution of defect frequency by type, wherein the defect pareto combines morphological and elemental information by dividing defects of the specific type based on morphology of the defects into multiple types depending on elemental information.

9. The apparatus of claim 8, wherein the instructions to perform the automated EDX review further comprise instructions to:
    move to a defect site;
    obtain an EDX spectrum from the defect site;
    move from the defect site to a reference site;
    obtain the EDX spectrum from the reference site; and generate a difference spectrum from the EDX spectrum from the defect site and the EDX spectrum from the reference site.

10. The apparatus of claim 9, wherein the defect site is indicated to be in an array of repeating cells, and wherein the instructions to move from the defect site to the reference site comprises instructions to deflect a primary electron beam by a cell dimension in one direction.

11. The apparatus of claim 9, wherein the defect site is indicated to be in a non-array patterned structure, and wherein the instructions to perform the automated EDX review further comprise instructions to:
  use electron-beam imaging to obtain a first image of area encompassing the defect site on the defective die;
  use electron-beam imaging to obtain a second image of an area encompassing the reference site on an adjacent die; and
  determine a location of the reference site in the second image after aligning the second image to the first image.

12. The apparatus of claim 11, wherein the instructions to move from the defect site to the reference site comprises instructions to translate the stage holding the target substrate so as to move a field of view of the SEM from the defect site on the defective die to the reference site on the adjacent die.

13. The apparatus of claim 9, wherein the instructions to perform the automated EDX review further comprise instructions to:
  derive elemental information from the difference spectrum for each defect of the specific type.

14. The apparatus of claim 8, wherein the defect pareto comprises a bar graph of defect frequency versus type.

15. The method of claim 1, wherein the defect pareto distinguishes between holes, scratches and particles and further distinguishes between fall-on particles of a first composition and fall-on particles of a second composition.

16. The apparatus of claim 8, wherein the defect pareto distinguishes between holes, scratches and particles and further distinguishes between fall-on particles of a first composition and fall-on particles of a second composition.

\* \* \* \* \*